United States Patent [19]

Abd-El-Aziz et al.

[11] Patent Number: 6,072,054
[45] Date of Patent: Jun. 6, 2000

[54] CYCLIC ARYL ETHERS, THIOETHERS, AND AMINES AND METHOD PREPARATION

[75] Inventors: Alaa S. Abd-El-Aziz; Christine R. de Denus; Leslie J. May, all of Winnipeg, Canada

[73] Assignee: University of Winnipeg, Canada

[21] Appl. No.: 09/233,533

[22] Filed: Jan. 20, 1999

[51] Int. Cl.[7] .................. C07C 321/04; C07C 321/30; C07C 381/04; C07D 211/14
[52] U.S. Cl. ................. 546/11; 546/190; 546/191; 568/49; 568/50; 568/53
[58] Field of Search ................ 546/190, 191, 546/11; 568/49, 50, 53, 585, 635

[56] References Cited

U.S. PATENT DOCUMENTS

| 4,105,636 | 8/1978 | Taylor . |
| 4,980,453 | 12/1990 | Brunelle et al. . |
| 5,110,893 | 5/1992 | Fukuyama . |
| 5,232,797 | 8/1993 | Moulton et al. . |
| 5,235,019 | 8/1993 | Savariar . |

OTHER PUBLICATIONS

Sheppodd et al., J. Am. Chem. Soc., 110(6) 1983–1985, 1988.
Cotrait et al., J. Chem. Res., Synop., 6, 206–207. 1993.
Baldoli et al., "Aromatic Nucleophilic Substitution of $Cr(CO)_3$–Complexed Halogenoarenes: A New Entry to Dibenzo Crown Ethers," *J. Chem. Soc. Chem. Commun.*, pp. 1181–1182 (1985).
Abd–El–Aziz et al., "Bis(cyclopentadienyliron)arene Complexes: A New Route to the Synthesis and Functionalization of Polyaromatic Ethers," *Organometallics*, 13:374–384 (1994).
An et al., "Novel Benzene–Bridged Macrobi–and Macrotricyclic Polyethers," *J. Org. Chem.*, 58:7694–7699 (1993).
Inoue et al., "Molecular Design of Crown Ethers: 12.[1] Complexation Thermodynamics of 12–to 16–Crown–4: Thermodynamic Origin of High Lithium Selectivity of 14–Crown–4," *J. Org. Chem.*, 58:5411–5413 (1993).
Mullins et al., "Opening Rings to Polyethers. Aromatic Macrocyclic Ethers Are Low Melt Viscosity Precursors to Linear Poly(arylethers). Use Them in Composites," *Chemtech*, pp. 25–28 (1993).
Abd–El–Aziz et al., "Controlled Design of Oligomeric Ethers with Pendant Cyclopentadienyliron Moieties," *J. Chem. Soc. Dalton Trans.*, pp. 3375–3393 (1995).
Janetka et al., "Synthesis of Peptidyl Ruthenium π–Arene Complexes: Application to the Synthesis of Cyclic Biphenyl Ether Peptides," *J. Am. Chem. Soc.*, 117:10585–10586 (1995).
Pearson et al., "Selective Arylation of Diols Using Arene–Iron Chemistry," *J. Org. Chem.*, 60:281–284 (1995).
Abd–El–Aziz et al., "Synthesis and Structural Characterization of Cyclic Aryl Ethers," *Chem. Commun.*, pp. 265–266 (1998).
Mullins et al., "Synthesis and Polymerization of Aryl Ether Cyclooligomers," *Polymer Preprints: Am. Chem. Soc. Div. Polymer Chem.*, 32:174–175 (1991).
Cozan et al., "Arylidene Copolyether Sulfones. I. Synthesis and Characterization of Some New Copolyether Sulfones Containing Dibenzylidene Cyclopentanone Moieties," *J.M.S.—Pure Appl. Chem.*, A30(12):899–906 (1993).

*Primary Examiner*—Joseph McKane
*Assistant Examiner*—Taofiq A. Solola
*Attorney, Agent, or Firm*—Nixon Peabody LLP

[57] ABSTRACT

Cyclic aryl ethers, thioethers or amines, and methods for synthesis are disclosed. These cyclic aryl compounds are synthesized by combining a first dinucleophile with a substituted benzene metallized electron-withdrawing complex, having halo or nitro substituen groups, to form a linear bimetallized aryl compound. The linear bimetallized aryl compound is then reacted with a second dinucleophile to form a cyclic bimetallized aryl compound. The metallized electron-withdrawing moieties are then removed from said cyclic bimetallized aryl compound by photolytic demetallation to form a cyclic aryl compound having the formula:

Formula (II)

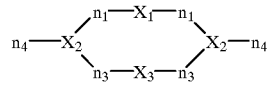

wherein:

$X_1$ and $X_3$ are the same or different and each is a alkyl, heteroalkyl, heterocyclic or aromatic group having up to 6 conjugated rings, optionally substituted;

$X_2$ is benzene $n_1$ and $n_3$ are the same or different and each is O, S or N; and $n_4$ is H or lower alkyl.

4 Claims, 2 Drawing Sheets

CYCLIC ARYL ETHERS, THIOETHERS, AND AMINES AND METHOD PREPARATION

The present invention relates to novel cyclic aryl compounds, particularly ethers, thioethers, and amines, and to a method for the preparation of these cyclic aryl compounds.

BACKGROUND OF THE INVENTION

Interest in the development of new polyaromatic ethers, thioethers, and amines, and routes for the synthesis of such compounds is increasing because of the useful chemical and physical properties they possess.

Polyaromatic ethers, thioethers and amines belong to a class of materials known as engineering thermoplastics, which are known to have desirable characteristics such as thermooxidative and dimensional stability, good mechanical properties, and resistance to high energy radiation. These materials are also known to be tough, creep resistant, and to exhibit good flexural, and tensile properties. Aromatic polymers find application in mouldings, coatings, adhesives, membranes and composite matrices.

Conventional cyclic polyethers are important synthetic targets owing to their ability to selectively complex ions. Interest in these materials originates from the size and nature of their cavity, which dictates whether or not such materials are capable of binding to compounds. Although a great deal of attention has been directed toward the encapsulation abilities of conventional cyclic polyethers, there is a growing interest in the synthesis of cyclic aryl ethers (see, for example An et al., *J. Org. Chem*, 1993:58:7694; Inoue et al., *J. Org. Chem.*, 1993, 58:5411; Janetka et at. *J. Am. Chem. Soc.* 1995:117:1058–10586). Cyclic aryl ethers are appealing since the rigidity and stability of their structures greatly reduces the compound's conformational freedom which may allow for chiral recognition or catalysis at high temperature or in hostile environments (Mullins et al., CHEMTECH August 1991:25). Mullins et at. (*Polym. Preprints: Am. Chem. Soc. Div. Polym. Chem.* 1991;32:174) reported that cyclic aryl ethers may be subjected to ring-opening polymerization to produce linear polyethers without the release of side-products.

Conventional cyclic polyether, thioether, and amine syntheses for the formation of macrocyclic compounds require the implementation of harsh reaction conditions in order to obtain the desired products in low yields. For nucleophilic aromatic substitution reactions, the presence of a strong electron-withdrawing group attached to a haloarene disadvantageously requires subsequent harsh chemical reactions to remove the electron-withdrawing group once the reaction is complete, which may lead to destruction of the product formed.

Known methods for preparation of aromatic polyethers include the Ullmann ether synthesis, the Scholl reaction, nickel-catalysed homocoupling, conventional nucleophilic aromatic substitution, and polycondensation (for example, Cozan et al., *J. Macromol. Sci. Pure Appl. Chem.*, 1993, 30:899). These methods may employ elevated temperatures, copper salts or oxides as catalysts, and in some cases, electron-withdrawing groups are bound to a reactant as required to force the reaction. These factors, along with the low reaction yield in some of these methods have resulted in a demand for a more efficient synthetic strategy.

The complexation of chloroarene to a metallic moiety in the activation of the aromatic ring toward nucleophilic aromatic substitution is known (see Pearson et al., *J. Org. Chem.* 1995; 60:281–284). This methodology enables preparation of a number of oligomeric ethers, thioethers and amines under mild reaction conditions. Abd-El-Aziz et al. (*Organometallics* 1994;13:374 and *J. Chem Soc. Dalton Trans* 1995:3375) provide reports of synthetic strategies for preparing linear aryl ethers using dichlorobenzene cyclopentadienyl iron complexes. A chain having up to 35 pendent cyclopentadienyl iron moieties has been reported. However, these synthetic routes are not capable of easily forming cyclic aryl ethers, thioethers or amines.

Crown ethers are an example of known cyclic aryl ethers. The preparation of dibenzo crown compounds is achieved via the nucleophilic aromatic substitution reactions of (o-dichlorobenzene)-Cr(CO)$_3$ with diethylene glycol and bis(2-mercaptoethyl) ether (Baldoli et al; *J. Chem. Soc. Chem Common.* 1985:1181). Disadvantages of this particular synthetic method are the implementation of harsh reaction conditions and the need for a phase-transfer catalyst in order to obtain the desired products in rather modest yields.

SUMMARY OF THE INVENTION

An object of the invention is to provide a method for the preparation of cyclic aryl compounds which obviates or mitigates one or more of the above-noted deficiencies in prior art methods.

A further objective of the invention is to provide novel cyclic aryl compounds and cyclic bimetallized aryl compounds, particularly cyclic aryl ethers, thioethers and amines.

According to the invention, there is provided a method for synthesis of a cyclic aryl compound according to Formula II:

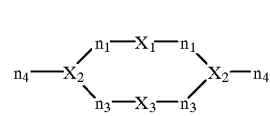

(Formula II)

wherein $X_1$ and $X_3$ are the same or different and are each:
(a) an aromatic structure having up to 6 conjugated rings which may be heteroaryl having C, N or S atoms, and which may include $C(CH_3)_2$, $SO_2$, S—S, or CO or $C_{1-6}$ alkyl in the structure or as substituents;
(b) a linear or branched alkyl group having from 3 to 12 carbons which may contain S;
(c) a cyclic alkyl having from 5 to 12 carbons; or
(d) a heterocyclic alkyl having C, S, or N;

$X_2$ is benzene;

$n_1$ is O, S or N, and when $n_1$ is N it may be combined with $X_1$;

$n_3$ is O, S or N, and when $n_3$ is N it may be combined with $X_3$; and $n_4$ is H or $C_{1-6}$ alkyl;

comprising the steps of:
(a) reacting a first dinucleophile of the formula:

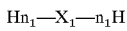

wherein $X_1$ and $n_1$ are as defined above;
with a substituted benzene metallized electron-withdrawing complex of the formula:

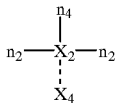

wherein:
$X_2$ and $n_4$ are as defined above;
$X_4$ is cyclopentadienyl metal or tricarbonyl metal; and
$n_2$ is halo or nitro; to form a linear bimetallized aryl compound of the formula:

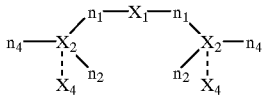

(b) reacting said linear birnetallized aryl compound with a second dinucleophile of the formula:

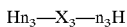

wherein $X_3$ and $n_3$ are as defined above, to form a cyclic bimetallized aryl compound according to Formula I;

Formula I

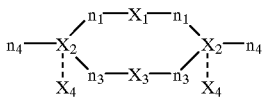

wherein $X_1$, $X_2$, $X_3$, $X_4$, $n_1$, $n_3$ and $n_4$ are as defined above;
(c) removing $X_4$ from the compound of Formula I to form the cyclic aryl compound of Formula II.

Further, according to the invention, there is provided a cyclic bimetallized aryl compound having the formula:

Formula (I)

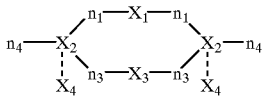

and a cyclic aryl compound having he formula:

Formula (II)

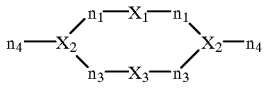

wherein $X_1$, $X_2$, $X_3$, $X_4$ and $n_1$, $n_3$ and $n_4$ are as defined above.

Advantageously, the method according to the invention allows preparation of a variety of cyclic aryl compounds under mild reaction conditions and in very high yields. Additionally, this method permits isolation of the intermediate bimetallic complex of Formula I after ring closure.

Additionally, it is possible to prepare both symmetric and asymmetric cyclic aryl compounds depending on the structure of the second nucleophile used to close the cyclic compound.

BRIEF DESCRIPTION OF THE DRAWINGS

These and other features of the invention will become more apparent from the following description in which reference is made to the appended drawings wherein.

DESCRIPTION OF PREFERRED EMBODIMENTS

Figure 1:
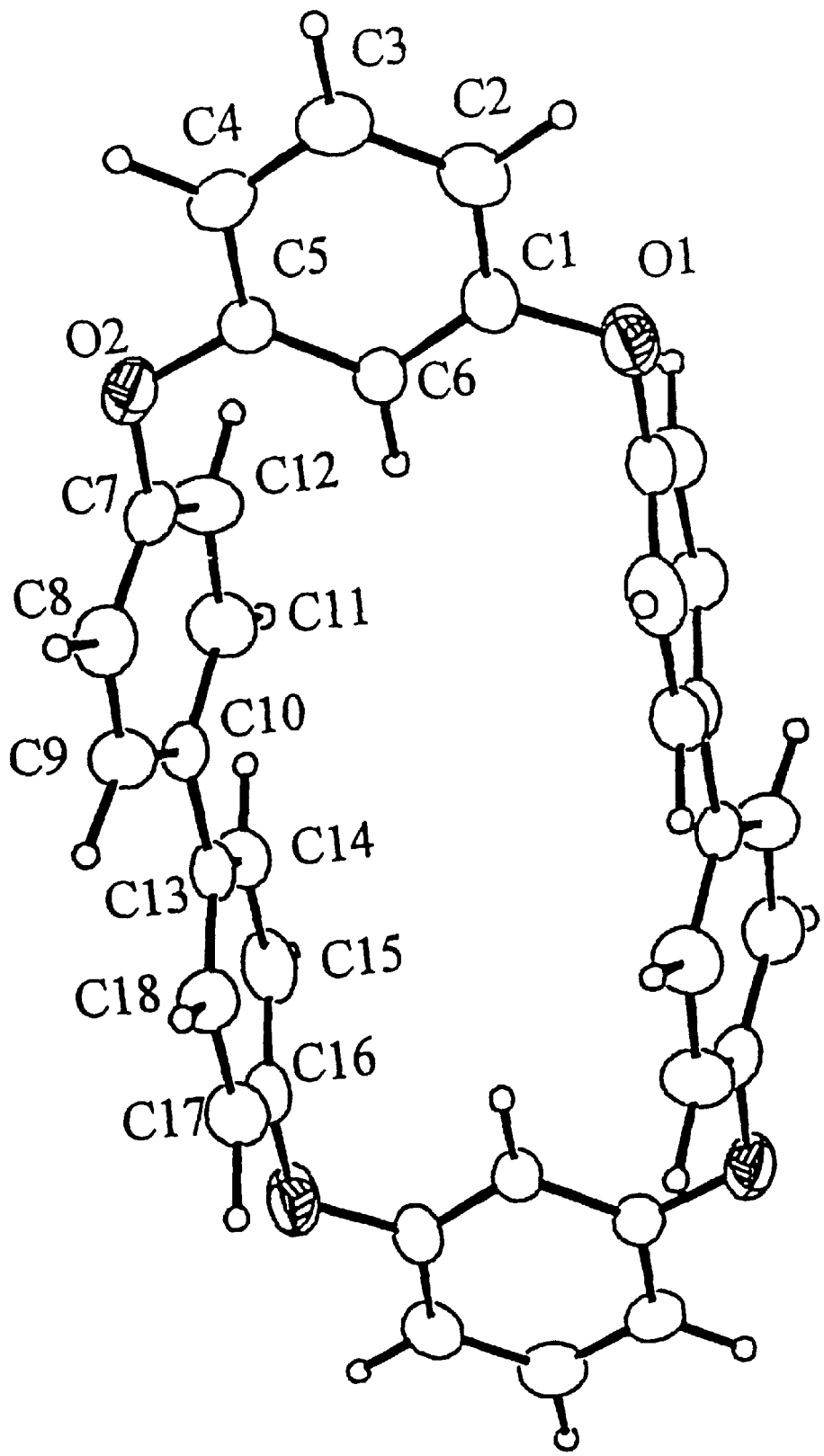
FIG. 1 is an ORTEP plot of a cyclic aryl ether according to Formula II-1.

The present invention relates to cyclic aryl compounds and cyclic aryl bimetallized compounds which are ethers, thioesters or amines, and to a method for synthesis of these compounds.

The Substituted Benzene Metallized Electron-Withdrawing Complex

The substituted benzene metallized electron-withdrawing complex comprises a benzene ring which is disubscituted with either halo or nitro groups, and may additionally be substituted with a $C_{1-6}$ alkyl group. The substituted benzene ring is complexed to a metallized electron-withdrawing group comprising a metal ion and an organic group having a strong electron-withdrawing function.

The benzene ring portion of the substituted benzene metallized electron-withdrawing complex has halo or nitro substituent groups at benzene ring positions 1,2-; 1,3-; or 1,4-. The positioning of the substituent groups used depends on the type of nucleophiles used in the linkages. If the nucleophiles contain large groups, such as aromatic groups, the subscituents are in the 1,3- or 1,4-positions. If the nucleophiles contains smaller groups, such as aliphatic linkages, the substituents are in the 1,2- or 1,3-positions. The substituent groups may be halo, for example chlorine, fluorine, bromine, or iodine, or may be nitro. Optionally, the benzene ring may be additionally substituted at one of the remaining carbon positions with a lower alkyl group ($C_{1-6}$).

In one embodiment of the present invention the benzene ring is substituted two chlorines and thus the substituted benzene i s either 1,2-dichorobenzene; 1,3-dichlorobenzene; or 1,4-dichlorobenzene.

The metallized electron-withdrawing group contains a metal which is complexed to the substituted benzene ring, and a strong electron-withdrawing organic group, such as cyclopentyldienyl or tricarbonyl. The metal ion can be, for example, $Fe^+$, $Mn^+$, $Cr^+$, or $Ru^+$.

Suitable examples of the metallied electron-withdrawing groups include but are not limited to cyclopentadienyl metal complexes, such as cyclopentadienyl iron (denoted in formulae as either $CpFe^+$ or $Fe^+Cp$), cyclopentadienyl ruthenium, cyclopentadienyl chromium, and cyclopentadienyl magnesium, or tricabonyl metal complexes, such as manganese tricarbonyl, and chromium tricarbonyl.

The metal ion is complexed to the substituted benzene and can be accompanied by a counter ion such as, for example but not limited to $[PF_6]^-$, $[BF_4]^-$, $[B(C_6H_5)_4]^-$, $[I_3]^-$, $[Br_3]^-$, $[BI_4]^-$, $[OTf]^-$, or picrate.

First Dinucleophile

The first dinucleophile can be any of the following:

(a) an aromatic structure having up to 6 conjugated rings which may be heteroaryl having C, N or S atoms, and which may include $C(CH_3)_2$, $SO_2$, S—S, or CO or $C_{1-6}$ alkyl in the structure or as substituents;

(b) a linear or branched alkyl group having 3 to 12 carbons which may contain S;

(c) a cyclic alkyl having from 5 to 12 carbons; or (d) a heterocyclic alkyl having C, S, or N; having OH, SH or NH at the two nucleophilic positions. When NH is present at the nucleophilic position, the N may comprise part of a ring structure, Examples of the first nucleophile include, but are not limited to the following:

HO—$(C_6H_4)_2$—OH

HO—$(C_6H_4)C(CH_3)_2(C_6H_4)$—OH

HO—$(C_6H_4)SO_2(C_6H_4)$—OH

HO—$C(C_6H_4)_4$—OH

HO—$C_{10}H_8$—OH

HO—$C_{10}H_6$—$S_2$—$C_{10}H_6$—OH

HO—$(C_6H_4)CO(C_6H_4)$—OH

HS—$(CH_2)_2S(CH_2)_2SH$

HS—$(CH_2)_2O(CH_2)_2SH$ or $(HNC_5H_9)(CH_2)_3(C_5H_9NH)$.

The Second Dinucleophile

The second dinucleophile may be the same as or different from the first dinucleophile, and can be any of the following:

(a) an aromatic structure having up to 6 conjugated rings which may be heteroaryl having C, N or S atoms, and which may include $C(CH_3)_2$, $SO_2$, S—S, or CO or $C_{1-6}$alkyl in the structure or as substituents;

(b) a linear or branched allyl group having 3 to 12 carbons which may contain S;

(c) a cyclic alkyl having from 5 to 12 carbons; or (d) a heterocyclic alkyl having C, S, or N;

having OH, SH or NH at the two nucleophilic positions. When NH is present at the nucleophilic position, the N may comprise part of a ring structure.

Examples of the second dinucleophile include, but are not limited to the following:

HO—$(C_6H_4)_2$—OH

HO—$(C_6H_4)C(CH_3)_2(C_6H_4)$—OH

HO—$(C_6H_4)SO_2(C_6H_4)$—OH

HO—$C(C_6H_4)_4$—OH

HO—$C_{10}H_8$—OH

HO—$C_{10}H_6$—$S_2$—$C_{10}H_6$—OH

HO—$(C_6H_4)CO(C_6H_4)$—OH

HS—$(CH_2)_2S(CH_2)_2SH$

HS—$(CH_2)_2)_2O(CH_2)_2SH$ or $(HNC_5H_9)(CH_2)_3(C_5H_9NH)$.

Preparation of a Linear Bimetallized Aryl Compound

By reacting a first dinucleophile with a substituted benzene metallized electron-withdrawing complex, a linear bimetallized aryl compound is formed.

The ratio of the first dinucleophile to the substituted benzene metallized electron-withdrawing complex can range from about 1:1 to about 1:5 during the reaction. Both nucleophilic sites on the first dinucleophile react with a halo- or nitro-substituted site of the substituted benzene to form a bond. As a result, two substituted benzene metallized electron-withdrawing complexes are bound to each first dinucleophile by an ether, thioether or amine bond, for nucleophilic sites having —OH, —SH, or —NH, respectively. Thus, reactants are consumed in a ratio of 1:2. At reactant ratios less than 1:2, the yield of product will be reduced. At reactant ratios above 1:2, yield will be high relative to initial quantity of the first dinucleophile, but unreacted substituted benzene metallized electron-withdrawing complex will remain.

In the reaction of the first dinucleophile with the substituted benzene metallized electron-withdrawing complex, a counter ion to each substituted benzene metallized electron-withdrawing complex is present, as discussed above. The product of this reaction is a linear bimetallized aryl compound, which may be an ether, thioether or amine. Reaction conditions in the formation of this product are discussed in the prior art, for example, Abd-El-Aziz et al., *J. Chem. Soc. Dalton Trans.* 1995:3375 and Abd-El-Aziz et al., *Organometallics* 1994;13:374–384.

The linear bimetallized aryl compound comprises the first nucleophile bound at both nucleophilic sites to the benzene ring of the benzene ring by an ether, thioether or amine linkage. The linear bimetallized aryl compound now contains the metallized electron-withdrawing group, for example a cyclopentadienyl iron, complexed via the metal group, in this example iron, to the benzene ring.

Preparation of a Cyclic Bimetallized Aryl Compound

To prepare a cyclic bimetallized aryl compound, the linear bimetallized aryl compound is reacted with a second dinucleophile.

Each linear bimnetallized aryl compound has two substituent groups remaining which are open to nucleophilic attack, one on each of the two benzene rings complexed with the metals. The second dinucleophile is of an appropriate size to conduct concurrent nucleophilic substitution at these two remaining substituent groups of the benzene rings. This reaction closes the linear polymer to form a cyclic bimetallized aryl compound.

The ratio of second dinucleophile to linear bimetallized aryl compound can range from about 0.5:1 to about 5:1 during the reaction. The reactants are consumed in a ratio of 1:1, and if insufficient quantities of the second dinucleophile are present, the yield will be low, relative to the amount of linear bimetallized aryl compound used. If excess quantities of the second dinucleophile are used, the yield will be high and unreacted quantities of the second dinucleophile will remain.

The formation of the cyclic bimetallized aryl compound occurs in the presence of a base, for example, but not to be construed as limiting, metal carbonates such as potassium carbonate, sodium carbonate, sodium hydride, sodium t-butoxide, potassium t-butoxide.

The reaction is conducted in any appropriate organic solvent, for example but not limited to dimethylfomirde, tetrahydrofuran, dimethylsulphoxide, dimethylformaxnide/ tetrahydofuran, dichloromethane, acetone, etc.

The reaction temperature can range from about 15° C. to about 70° C., and the reaction may be conducted for about 5 to about 30 hours. The reaction occurs under nitrogen or argon atmosphere.

The cyclic bimetallized aryl compound comprises the first nucleophile bound at both nucleophilic sites to benzene rings by an ether, thioether or amime linkage and also contains the second nucleophile bound at both nucleophilic sites to the benzene rings by an ether, thioether or amine linkage, at the formerly halo- or nitro-substituted carbons. The cyclic bimetallized aryl compound also contains the electron-withdrawing group, for example a cyclopentadienyl iron, complexed via the metal group, in this case iron, to both benzene rings.

To isolate and purify the cyclic bimetallized aryl compound, after conducting the reaction, the resulting solution can be poured into an aqueous solution of about 5% to about 20% strong acid (v/v) to precipitate the cyclic bimetallized aryl compound. The acid can be hydrochloric or sulfuric, for example.

An aqueous solution of counter ion salt may also be used to precipitate. the cyclic bimetallized aryl compound. The counter ion may be, for example but not limited to $[PF_6]^-$, $[BF_4]^-$, $[B(C_6H_5)_4]^-$, $[I_3]^-$, $[Br_3]^-$, $[BI_4]^-$, $[OTf]^-$, or picrate. An appropriate salt of the counter ion, such as the ammonium salt, is used.

The precipitated cyclic bimetallized aryl compound can then be collected, washed and dried as required or further purified according to standard methodology.

Preparation of a Cyclic Aryl Compound

To prepare the cyclic aryl compound, the metallized electron-withdrawing group is removed from both benzene rings of the cyclic metallized aryl compound formed as described above. The metallic portion of the metallized electron-withdrawing moiety is thereby de-complexed to the benzene ring.

Any acceptable means of removal of the metallized complex to the benzene ring may be used, such as, but not limited to, photolytic demetallation, thermolysis or electrolysis.

In the case of photolytic demetauation, the cyclic metallic aryl compound is dissolved in an organic solvent, for example acetnitrile, dinethylformamide, acetone, dimethylsulphoxide, or dichloromethane/acetonitrile mixture.

The solvent mixture is then irradiated with radiation in the UV-visible range, such as a Xenon lamp for a period of time ranging from about 2 to about 10 hours appropriate to achieve demetallation.

Isolation and Purification of the Cyclic Aryl Compound

Subsequently, the cyclic aryl compound produced is extracted from the solution, for example by solvent evaporation followed by further organic solvent extraction, such as by a chloroform/nitromethane mixture, dichloromethane, acetone, dimethylformamide, or dimethylsulphoxide extraction. The cyclic aryl compound could then be washed and filtered according to standard methodology The by-products of demetallation can be separated from the cyclic aryl compound using standard methodology, such as column chromatography, using hexane to elute such by-products as ferrocene, followed by chloroform or ethyl acetate elution of the cyclic aryl compound.

Utility

The cyclic aryl compounds formed according to the invention are usefull as macrocycles in studies of conformational analysis, Specifically, guest-host chemistry involves the recognition of the "guest" molecule by the "host" molecule. The rigidity of the macrocyclic "host" allows for the molecular recognition of the "guest" molecule. A given macrocycle only complexes to certain molecular conformations. Thus, for a guest to become complexed, it must possess the correct conformation.

The compounds of the present invention readily undergo ring-opening polymerization to yield a linear polymer. This is desirable because the resulting polymers are of high molecular weight and low polydispersity. Polydispersity is an indication of the amount of branching in a polymer and a low polydispersity indicates minimal branching. The less branching in a polymer, the stronger it is.

Compounds of the present invention are also appealing due to the rigidity and stability of the structures, which reduces conformational freedom, The molecules may be used in chiral recognition, by introducing a chiral center into the molecule to allow for identification of other chiral species through joining of the two molecules (complexation). Chiral recognition is beneficial for separating enantiomeric mixtures which cannot be separated using traditional methods, such as GC, HPLC, or column chromatography. Introducing a chiral center into a macrocycle of the present invention which possesses an appropriate cavity size, would enable separation of enantiomeric mixtures. These macrocycles may be used in selective complexation or as molecular receptors.

Compounds of the present invention may be useful as catalysts at high temperatures or in hostile environments, since the aromatic sub-units cause the macrocycle to be rigid and strong, thus enabling them to withstand harsh environments. As a harsh environment catalyst, the molecule would speed up reactions in environments in which other catalysts do not survive.

EXAMPLES

Examples are provided which describe particular embodiments of the invention. The examples are not to be construed as limiting. The invention encompasses such modifications to the exemplified embodiments as would occur to one skilled in the art.

Example 1

A first dinucleophile, $HO—(C_6H_4)_2—OH$, is combined with 1,3-dichlorobenzene cyclopentadienyl iron (II) hexafluorophosphate in a ratio of 1:2 to form a linear bimetallic aryl ether. The linear bimetallic aryl ether (0.5 mmol) is combined with 0.5 mmol of $HO—(C_6H_4)_2—OH$ (the second dinucleophile), 2.5 mmol of potassium carbonate ($K_2CO_3$), and 10 mL of dimethylformamide (DMF) in a 25 mL round bottom flask. The solution is then reacted at room temperature or refluxed at 65° C. under a nitrogen atmosphere for 20 to 24 hours.

The solution is poured into 50 mL of 10% (v/v) hydrochloric acid causing the cyclic bimetallic aryl ether to precipitate out of solution. Aqueous ammonium hexafluorophosphate ($NH_4PF_6$) is added to further aid precipitation of the product. The product is then collected using a glass crucible and washed with several portions of distilled water. After drying for several hours the product is rinsed with a small amount of diethyl ether, and is allowed to dry. The cyclic bimetallic aryl ether so formed is illustrated below as Formula I-1.

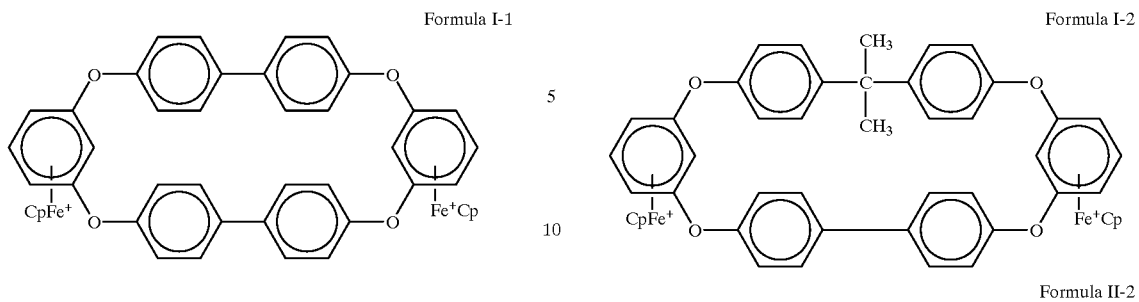

Formula I-1

Formula I-2

In a 50 mL Pyrex photolysis tube, 0.25 mmol of the cyclic bimetallic aryl ether is dissolved in 40 mL of a dichloromethane1acetonitrile ($CH_2Cl_2/CH_3CN$) mixture. This solution is then irradiated with a xenon lamp for 5–6 hours to achieve demetallation by photo decomposition. After this time, the solvent mixture is evaporated from the product leaving a black solid, which is then extracted with a chloroform/nitromethane ($CHCl_3/CH_3CN$) mixture and washed with distilled water. The organic layer is then dried with magnesium sulfate, gravity filtered into a 250 mL round bottom flask, and the solvent is evaporated off.

The cyclic aryl ether is then separated from the by-products of photolysis via column chromatography. Ferrocene, one of the by-products, is eluted from the column with hexane, followed by the elution of the cyclic aryl ether using chloroform ($CHCl_3$) and/or ethyl acetate ($CH_3COOCH_2CH_3$). The cyclic aryl ether product of Example 1 is illustrated below as Formula II-1.

Formula II-1

FIG. 1 represents the ORTEP plot of the product formed in Example 1, Formula II 1.

X-ray crystallography provides structural proof for the presence of the compound of Formula (II-1). Crystal data: colourless crystals from $CHCl_3$, crystal dimensions 0.40× 0.20×0.20 mm, monoclinic space group P2√c.a=6.0546(16), h=16.093(2), c=13.514(4) Å, V=1314.7(6)Å, Z=4 , $\mu$=0.07 $mm^{-1}$, 1814 reflections measured, 1736 unique, $R_w$=0.058, R=0.050, CCDC 182/696.

Example 2

The following products are prepared according to the method of Example 1.

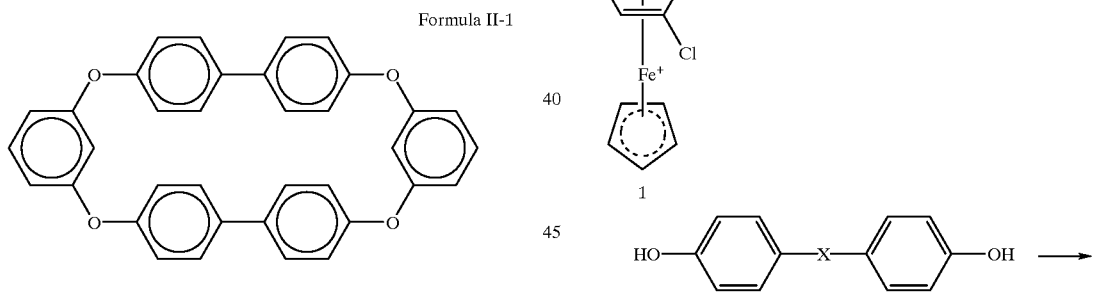

Formula II-2

SCHEME 1

Scheme 1 outlines the reaction sequence employed for the preparation of cyclic bimetallic aryl ethers of Formula I-1 and Formula I-2, and cyclic aryl ethers of Formula II-1 and Formula II-2 according to Examples 1 and 2.

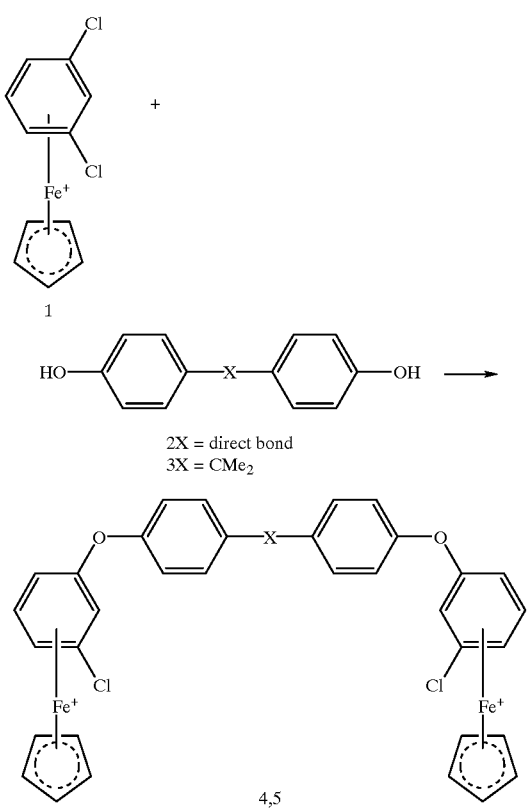

-continued

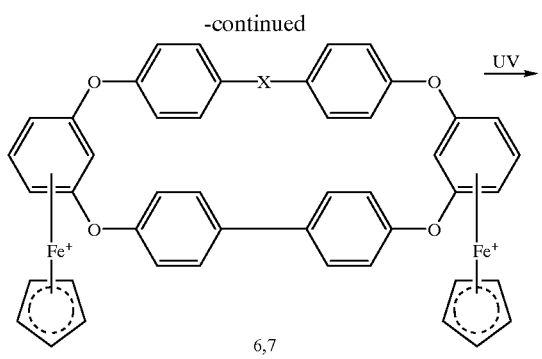

6,7

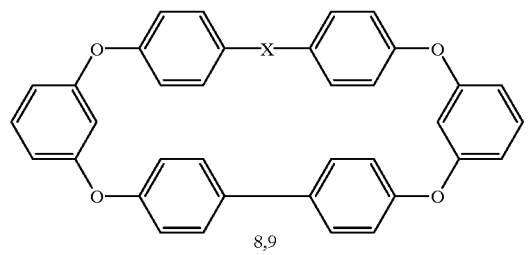

8,9

In this scheme, the initial reaction of complex 1 and dinucleophile 2 or 3 in a 2:1 molar ratio is carried out in order to obtain the bimetallic complex (4 or 5) in high yield. The reaction of 4 or 5 with dinucleophile 2 in an equimolar ratio leads to the formation of complexed cyclic aryl ethers Formulae I-1 and I-2 (denoted as 6 and 7) in yields of 86 and 89%, respectively.

The rigid nature of these complexed macrocycles introduces both cis- and trans-orientations of the cyclopentadienyl iron (CpFe$^+$) moieties attached to the arene ring. The presence of two different cyclopentadienyl (Cp) resonances as well as a complex aromatic region in the $^1$H NMR spectra indicates a mixture of both cis and trans products present. Based on the integration of the respective Cp resonances, it was determnied that for complex of Formula I-1 the ratio of cis to trans product was 3:1 while it was 1:1 for the complex of Formula I-2. The major structure was predicted to be trans based on previous findings.

Photolytic demetallation was implemented to allow for the recovery of the free organic macrocycles of Formulae II-1 and II-2 (here indicated as 8 and 9) in yields of 64 and 58%, respectively, which may be attributed to the poor solubility of these macrocyclic materials in most organic solvents, The $^1$H NMR spectra indicated the symmetric nature of these materials. It was noted that a triplet was present at a rather high field chemical shift of δ 5.6 (8) or 6.2(9) which was attributed to the inner-ring protons of the benzene ring. This shift is explained by the large diamagnetic shielding caused by the two adjacent biphenyl rings on the inner-ring protons. This observation is in accordance with similar cyclic aryl ether NMR shifts Unequivocal proof of the structure of 8 was obtained by an X-ray crystallographic study, as discussed above, Single crystals suitable for X-ray analysis were obtained by slow evaporation of a chloroform solution of the cyclic aryl ether at room temp. Rigidity imparted in the structure by the biphenyl and benzene rings of the compounds formed according to scheme 1. The biphenyl groups of the macrocycle are separated by 5.2 Å while the diagonal distance of oxygen atoms was found to be 10.9 Å.

Example 3

The following products are prepared according to the method of Example 1 with the appropriate selection of $X_1$, $X_3$, $n_1$ and $n_3$.

Formula I-3

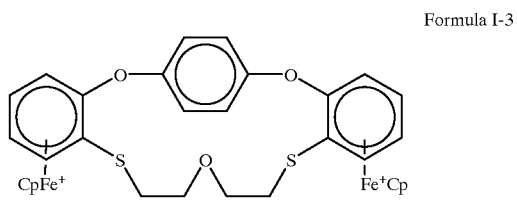

Formula II-3

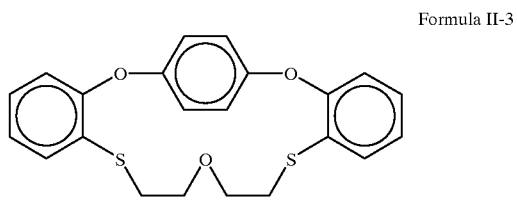

Example 4

The following products are prepared according to the method of Example 1 with the appropriate selection of $X_1$, $X_3$, $n_1$ and $n_3$.

Formula I-4

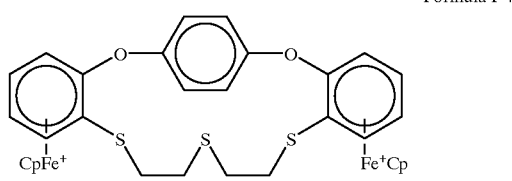

Formula II-4

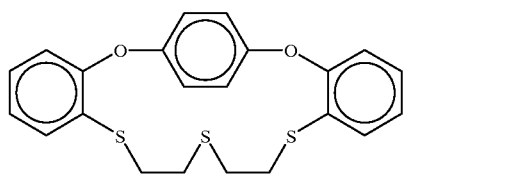

SCHEME 2

Scheme 2 illustrates the sequence of reactions may be employed with the (dichlorobenzene)CpFe+ complex (10) and dinucleophiles containing both aliphatic and aromatic bridges.

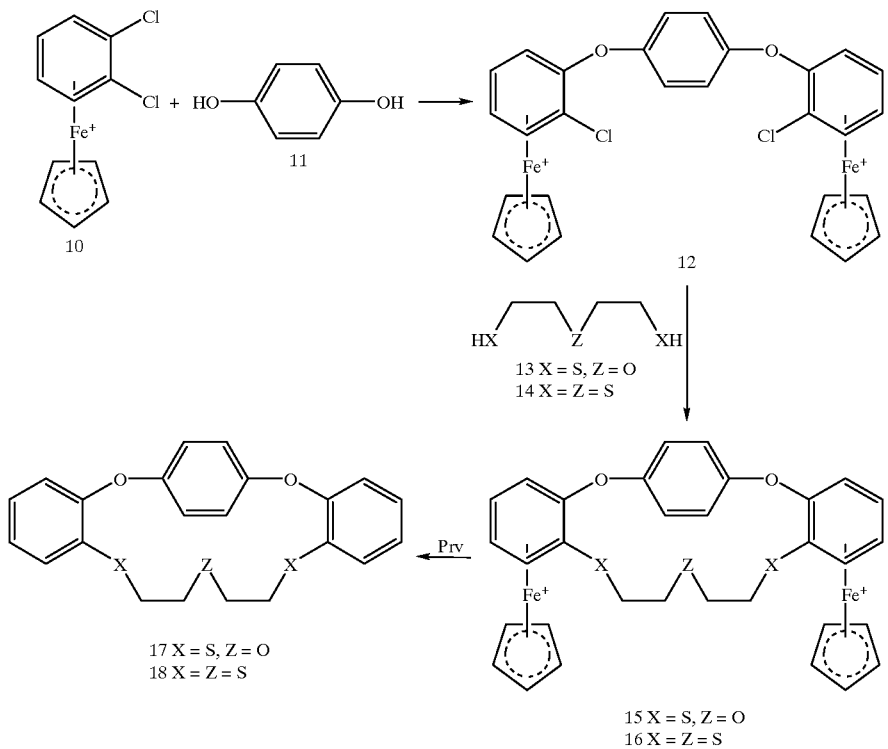

In this scheme, cyclic bimetallic aryl ether compounds 15 and 16 (corresponding to Formulae I-3 and I-4, respectively) and cyclic aryl ether compounds 17 and 18 (corresponding to Formulae II-3 and II-4, respectively) having both oxygen and sulfur bridges can be prepared. Unlike the rigid macrocycles prepared in Scheme 1 (Examples 1 and 2), these structures have no inner ring protons and as a result no high field chemical shifts were observed.

Specific examples of compounds formed by this process are shown in Examples 3 and 4. For each example, the cyclic bimetallic aryl ether and the (organic) cyclic aryl ether are illustrated

Example 5

The following products are prepared according to the method of Example 1 with the appropriate selection of $X_1$, $X_3$, $n_1$ and $n_3$.

Formula I-5

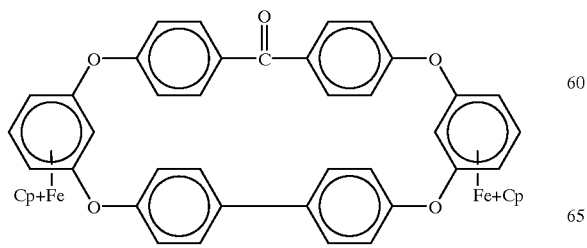

-continued

Formula II-5

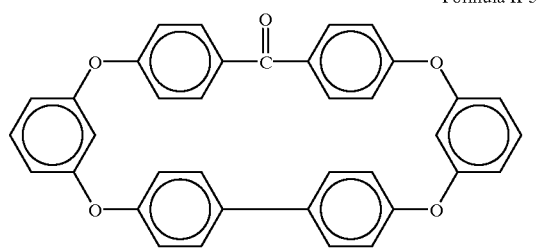

Example 6

Figure 2:
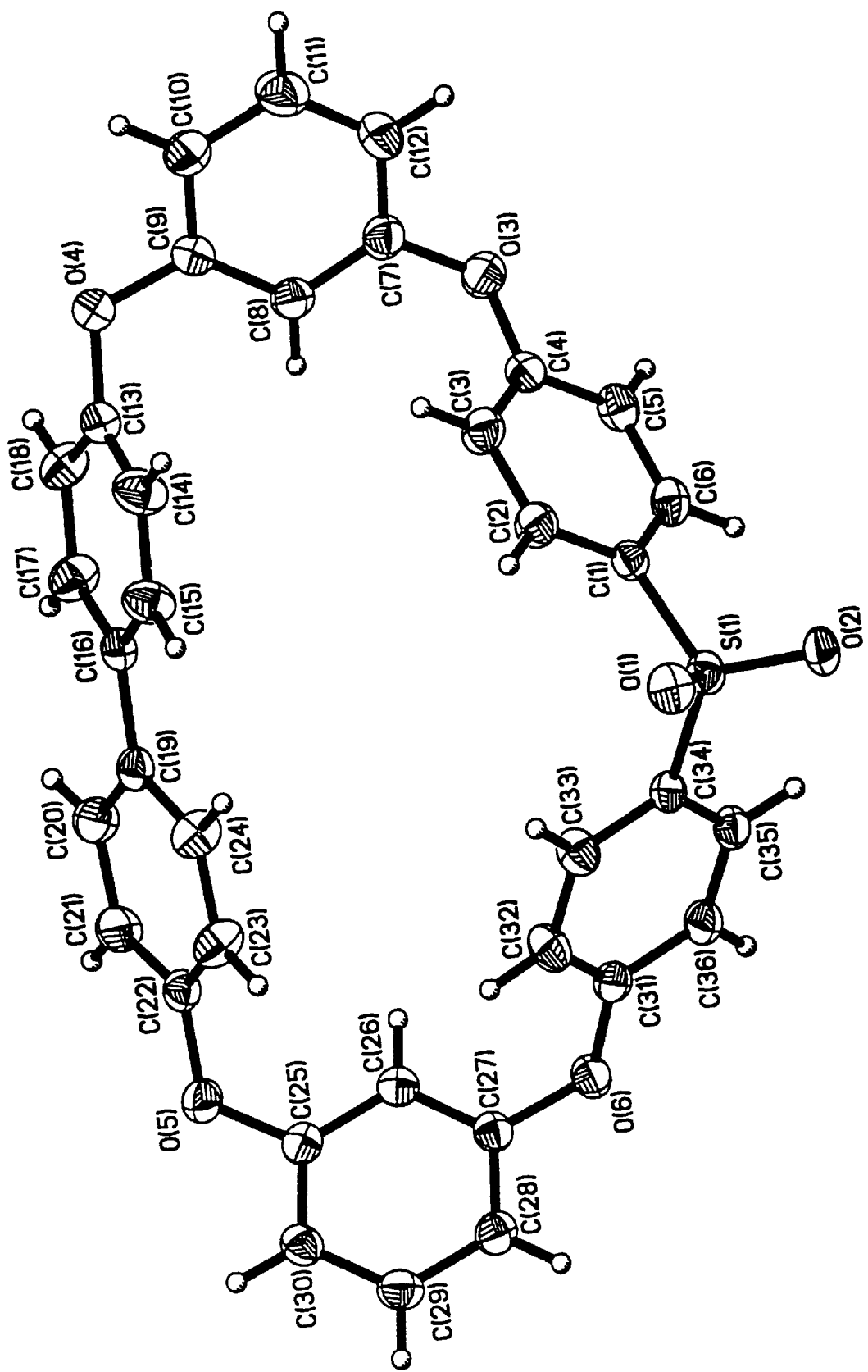
FIG. 2 is an ORTEP plot of a cyclic aryl ether according to Formula II-6.

The following products are prepared according to the method of Example 1 with the appropriate selection of $X_1$, $X_3$, $n_1$ and $n_3$. FIG. 2 represent the ORTEP plot of the compounds shown below as Formula II-6.

Formula I-6

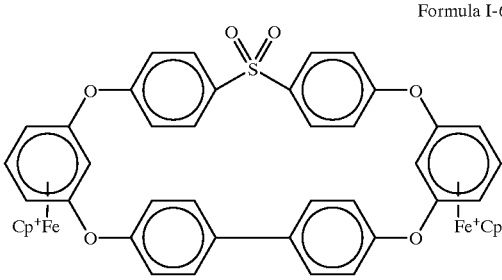

Formula II-6

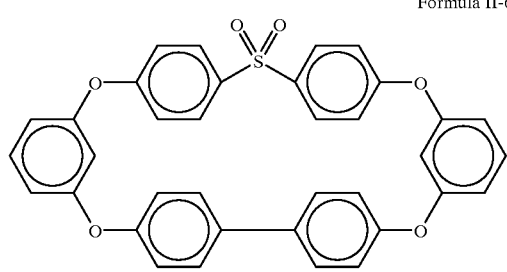

Example 7

The following products are prepared according to the method of Example 1 with the appropriate selection of $X_1$, $X_3$, $n_1$ and $n_3$.

Formula I-7

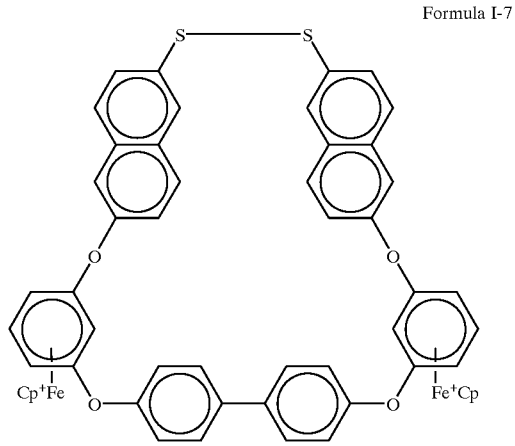

Formula II-7

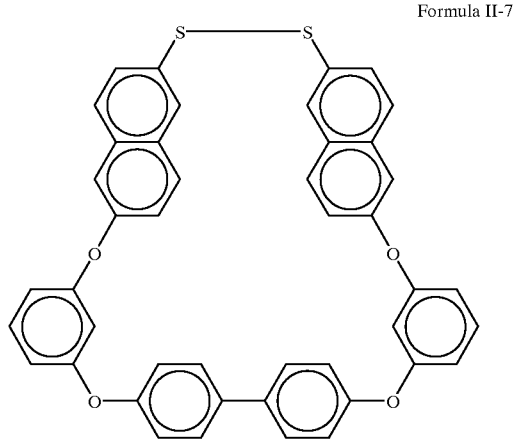

Example 8

The following products are prepared according to the method of Example 1 with the appropriate selection of $X_1$, $X_3$, $n_1$ ad $n_3$.

Formula I-8

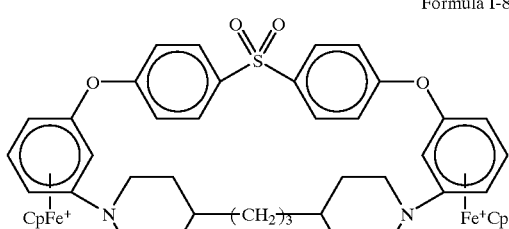

Formula II-8

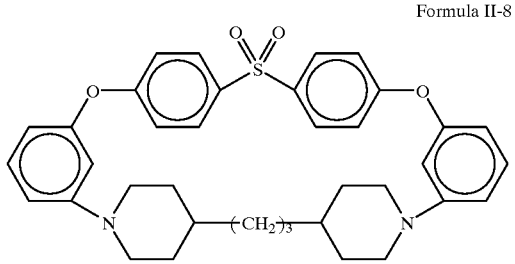

Example 9

The following products are prepared according to the method of Example 1 with the appropriate selection of $X_1$, $X_3$, $n_1$ and $n_3$.

Formula I-9

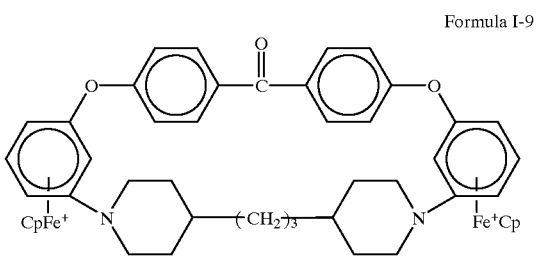

Formula II-9

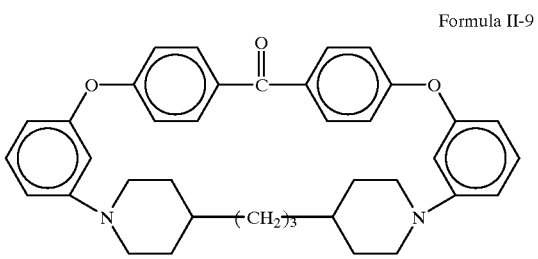

Example 10

The following products are prepared according to the method of Example 1 with the appropriate selection of $X_1$, $X_3$, $n_1$ and $n_3$.

Formula I-10

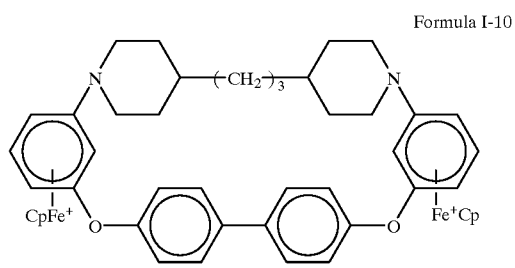

Formula II-10

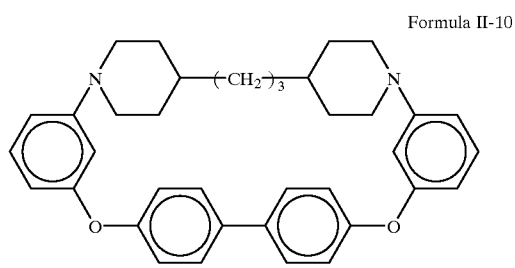

Example 11

The following products are prepared according to the method of Example 1 with the appropriate selection of $X^1$, $X_3$, $n_1$ and $n_3$.

Formula I-11

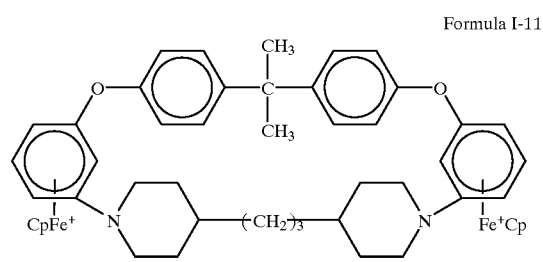

Formula II-11

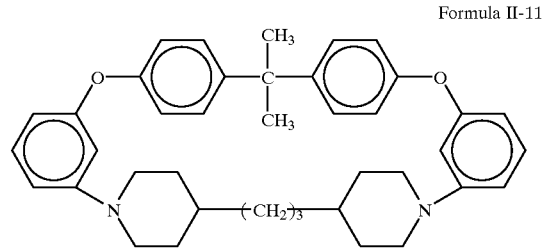

Example 12

The following products are prepared according to the method of Example 1 with the appropriate selection of $X_1$, $X_3$, $n_1$ and $n_3$.

Formula I-12

Formula II-12

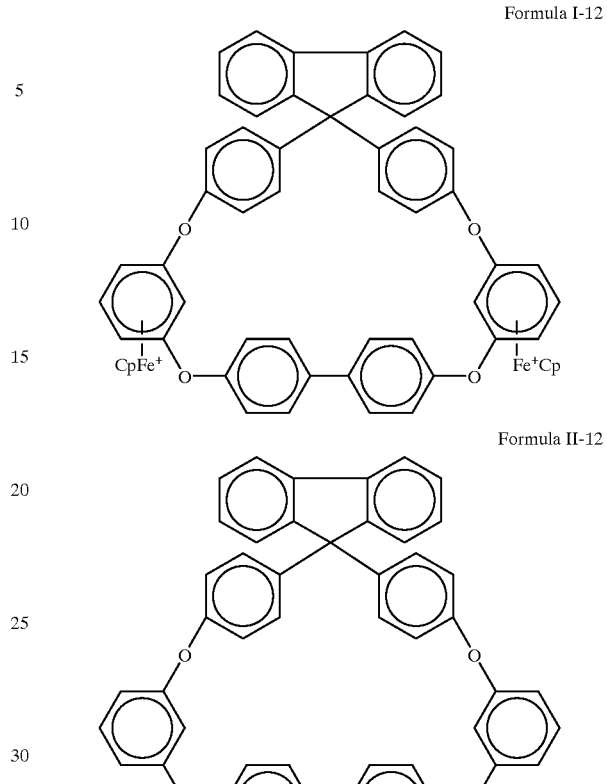

Example 13

The following product is prepared according to the method of Example 1 with the appropriate selection of $X_1$, $X_3$, $n_1$ and $n_3$.

Formula I-13

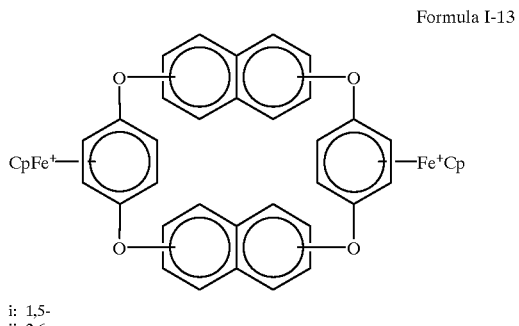

i: 1,5-
ii: 2,6-

All publications cited herein are incorporated by reference. Various modifications may be made without departing from the invention. It is understood that the invention has been disclosed herein in connection with certain examples and embodiments. However, such changes, modifications or equivalents as can be used by those skilled in the art are intended to be included. Accordingly, the disclosure is to be construed as exemplary, rather than limiting, and such changes within the principles of the invention as are obvious to one skilled in the art are intended to be included within the scope of the claims.

What is claimed is:

1. A cyclic bimetallized aryl compound having the following formula:

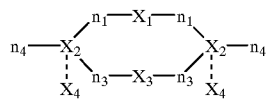

Formula I wherein:

$X_1$ and $X_3$ are the same or different and are each:
(a) an aromatic structure having up to 6 conjugated rings which may be heteroaryl having C, N or S atoms, and which may include $C(CH_3)_2$, $SO_2$, S—S, or CO or $C_{1-6}$ alkyl in the structure or as substituents;
(b) a linear or branched alkyl group having from 3 to 12 carbons which may have S;
(c) a cyclic alkyl having from 5 to 12 carbons; or
(d) a heterocyclic alkyl having C, S, or N;

$X_2$ is benzene;

$n_1$ is O, S or N, and when $n_1$ is N it may be combined with $X_1$;

$n_3$ is O, S or N, and when $n_3$ is N it may be combined with $X_3$; and $n_4$ is H or $C_{1-6}$ alkyl; and $X_4$ is cyclopentadienyl metal or tricarbonyl metal.

2. A cyclic bimetallized aryl compound according to claim 1, wherein:

$X_1$ and $X_2$ are the same or different and each is selected from the group consisting of:
$(C_6H_4)_2$
$(C_6H_4)C(CH_3)_2(C_6H_4)$
$(C_6H_4)SO_2(C_6H_4)$
$C(C_6H_4)_4$
$C_{10}H_8$
$C_{10}H_6—S_2—C_{10}H_6$
$(C_6H_4)CO(C_6H_4)$
$(CH_2)_2S(CH_2)$ and
$(CH_2)_2O(CH_2)_2$;

or $n_1$ or $n_3$ is N and is combined with $X_1$ or $X_3$, respectively, to form the group $(NC_5H_9)(CH_2)_3(C_5H_9N)$.

3. The cyclic bimetallized aryl compound according to claim 1, having a formula selected from the group consisting of:

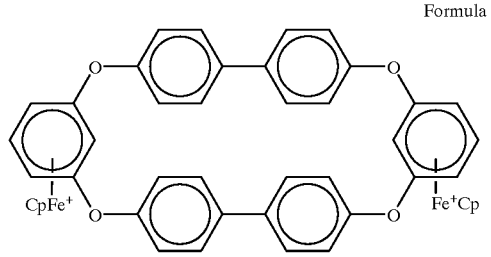

Formula I-1

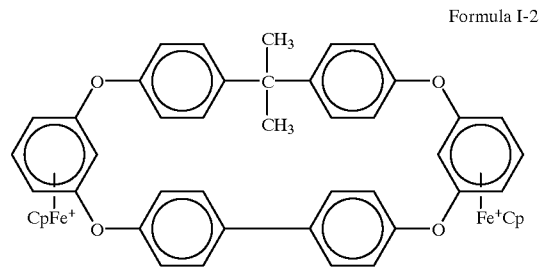

Formula I-2

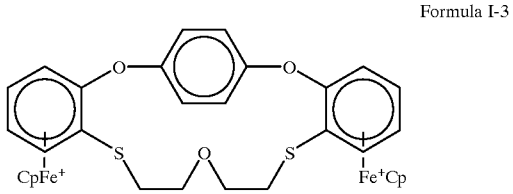

Formula I-3

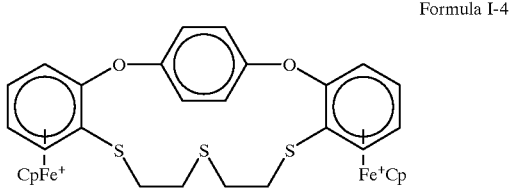

Formula I-4

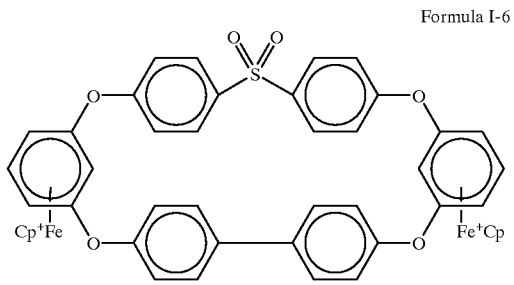

Formula I-6

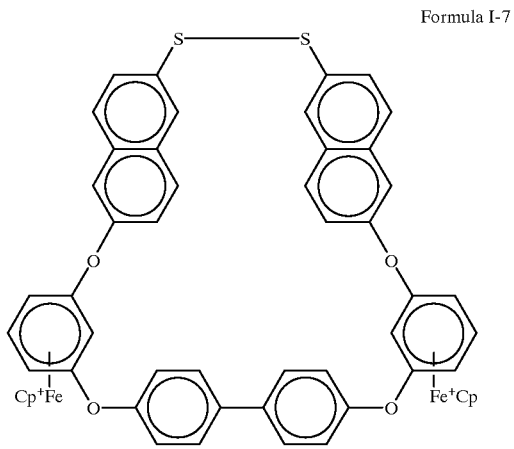

Formula I-7

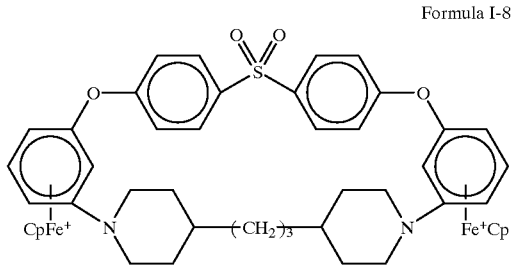

Formula I-8

-continued
Formula I-9
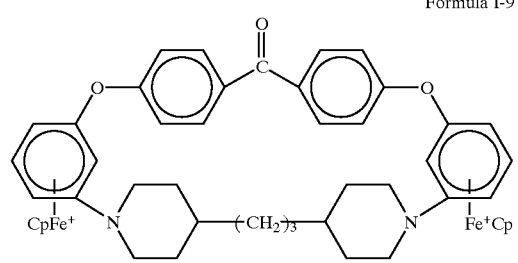
Formula I-10
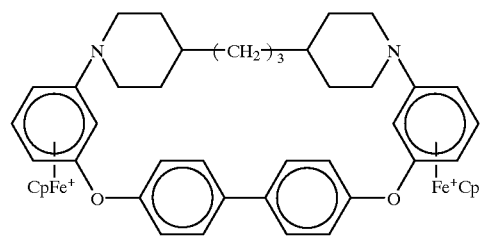
Formula I-11
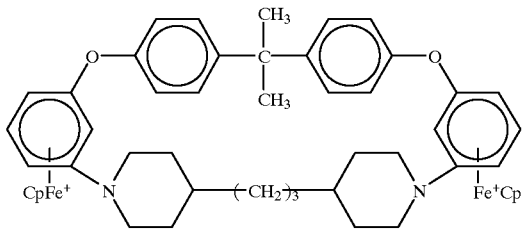
Formula I-12
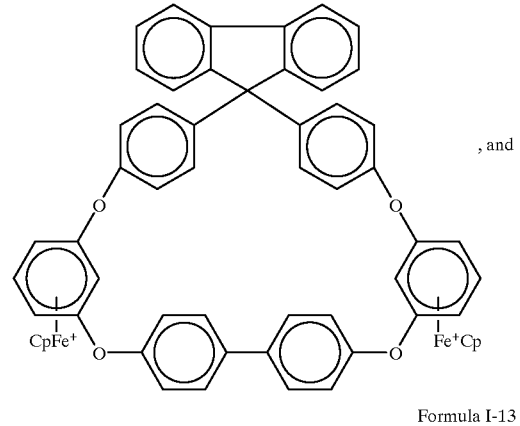
, and
Formula I-13
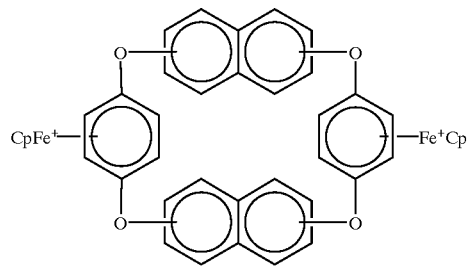
i: 1,5-
ii: 2,6-
4. A cyclic aryl compound having a formula selected from the group consisting of:
Formula II-1
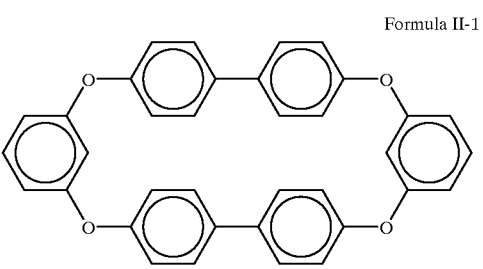
Formula II-2
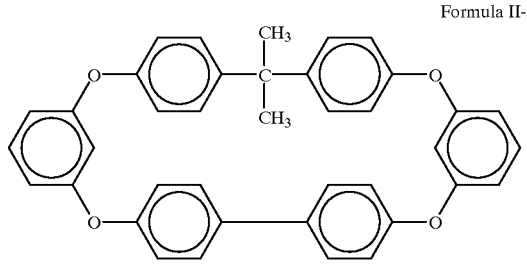
Formula II-3
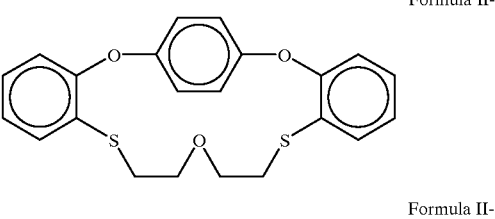
Formula II-4
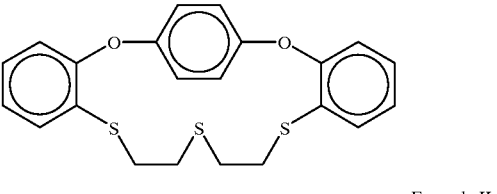
Formula II-5
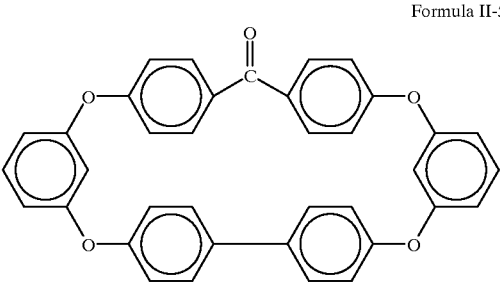
Formula II-6
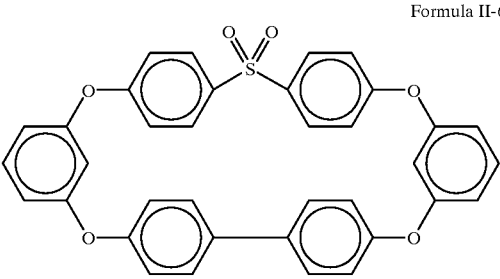

Formula II-7
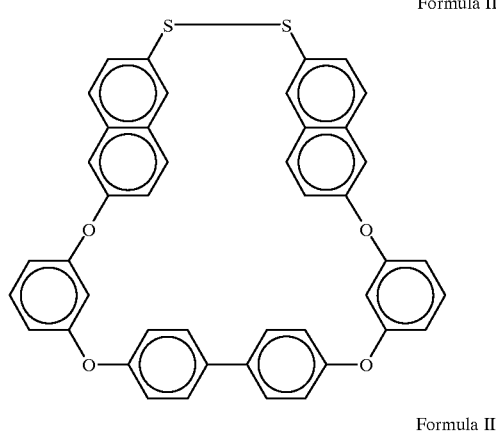
Formula II-8
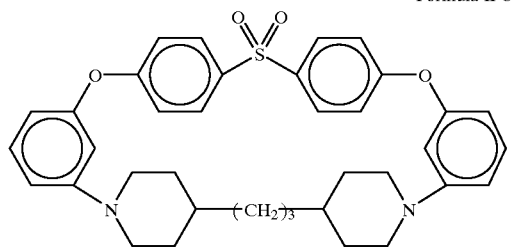
Formula II-9
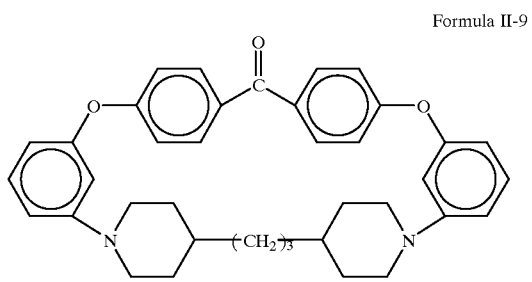
Formula II-10
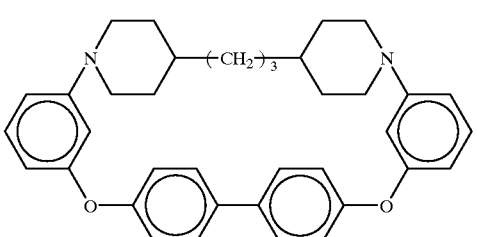
Formula II-11
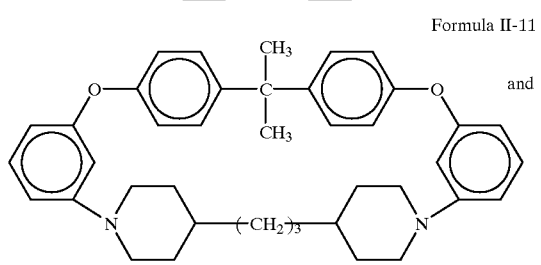
and
Formula II-12
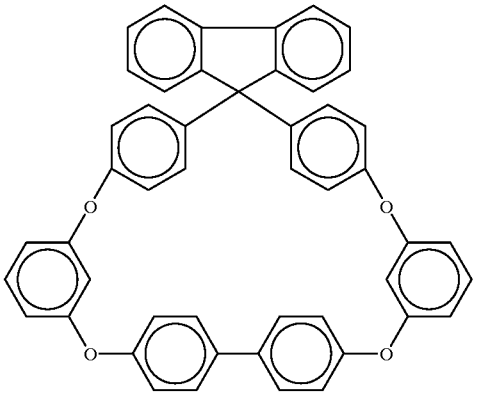
* * * * *